(12) United States Patent
Poigny et al.

(10) Patent No.: US 8,722,729 B2
(45) Date of Patent: May 13, 2014

(54) UNSATURATED FATTY ACID MONOESTERS AND DIESTERS ON ASCORBIC ACID AND COSMETIC USES THEREOF

(75) Inventors: Stéphane Poigny, Saubens (FR); Sylvie Daunes-Marion, Toulouse (FR); Nathalie Castex Rizzi, Colomiers (FR); Patrick Bogdanowicz, Balma (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 13/376,752

(22) PCT Filed: Jun. 8, 2010

(86) PCT No.: PCT/EP2010/057979
§ 371 (c)(1),
(2), (4) Date: Dec. 7, 2011

(87) PCT Pub. No.: WO2010/142663
PCT Pub. Date: Dec. 16, 2010

(65) Prior Publication Data
US 2012/0076744 A1 Mar. 29, 2012

(30) Foreign Application Priority Data
Jun. 8, 2009 (FR) .................. 09 53785

(51) Int. Cl.
*A01N 43/26* (2006.01)
*C07D 307/62* (2006.01)

(52) U.S. Cl.
USPC .................. 514/467; 549/317

(58) Field of Classification Search
USPC .................. 549/317
See application file for complete search history.

(56) References Cited

U.S. PATENT DOCUMENTS

| | | | |
|---|---|---|---|
| 2002/0042380 A1 | 4/2002 | Castiel et al. | |
| 2006/0039937 A1 | 2/2006 | Mujica-Fernaudd et al. | |
| 2007/0167517 A1* | 7/2007 | Kvitnitsky et al. | 514/474 |
| 2008/0287533 A1 | 11/2008 | Gupta | |

FOREIGN PATENT DOCUMENTS

EP 1145710 A1 10/2001

OTHER PUBLICATIONS

PCT/ISA/210—International Search Report dated Jul. 21, 2010 for PCT/EP2010/057979.
Bissett, "Glucosamine: an ingredient with skin and other benefits," Journal of Cosmetic Dermatology, vol. 5, 2006, pp. 309-315.
Botzki et al., "L-Ascorbic Acid 6-Hexadecanoate, a Potent Hyaluronidase Inhibitor," The Journal of Biological Chemistry, vol. 279, No. 44, Oct. 29, 2004, pp. 45990-45997.
Calder, "Polyunsaturated Fatty Acids, Inflammation, and Immunity," Lipids, vol. 36, No. 9, Sep. 2001, pp. 1007-1024.
Delpech et al., "Immunoenzymoassay of the Hyaluronic Acid-Hyaluronectin Interaction: Application to the Detection of Hyaluronic Acid in Serum of Normal Subjects and Cancer Patients," Analytical Biochemistry, vol. 149, 1985, pp. 555-565.
Fisher et al., "Pathophysiology of Premature Skin Aging Induced by Ultraviolet Light," N. Engl. J. Med., vol. 337, No. 20, 1997, pp. 1419-1428.
Frost et al., "A Microtiter-Based Assay for Hyaluronidase Activity Not Requiring Specialized Reagents," Analytical Biochemistry, vol. 251, 1997, pp. 263-269.
Hayflick, "The Cell Biology of Aging," The Journal of Investigative Dermatology, vol. 73, No. 1, 1979, pp. 8-14.
Kähäri et al., "Matrix metalloproteinases in skin," Exp. Dermatol., vol. 6, 1997, pp. 199-213.
Nagase et al., "Matrix Metalloproteinases," The Journal of Biological Chemistry, vol. 274, No. 31, Jul. 30, 1999, pp. 21491-21494.
Philpott et al., "Human hair growth in vitro," Journal of Cell Science, vol. 97, 1990, pp. 463-471.
Redoules et al., "Characterisation and Assay of Five Enzymatic Activities in the Stratum Corneum Using Tape-Strippings," Skin Pharmacol. Appl. Skin Physiol., vol. 12, 1999, pp. 182-192.

(Continued)

*Primary Examiner* — Frederick Krass
*Assistant Examiner* — Dennis J Parad
(74) *Attorney, Agent, or Firm* — Birch, Stewart, Kolasch & Birch, LLP

(57) ABSTRACT

The present invention relates to a compound with the following general formula (I):

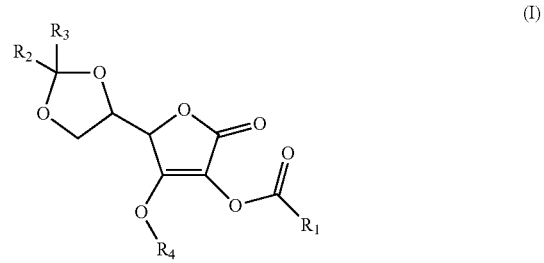

in which: $R_1$ is a hydrocarbon chain of an unsaturated fatty acid from $C_{12}$ to $C_{24}$ including at least one unsaturation; and $R_2$ and $R_3$ are, independently or simultaneously: a hydrogen or a $C_1$-$C_3$ alkyl or a phenyl; and $R_4$: a hydrogen atom or $COR_{1'}$, where $R_{1'}$ is a hydrocarbon chain of an unsaturated fatty acid from $C_{12}$ to $C_{24}$ including at least one unsaturation, advantageously 1 to 6 and preferably 1 to 4.

6 Claims, 2 Drawing Sheets

(56) References Cited

OTHER PUBLICATIONS

Ren et al., "Anti-inflammatory Effect of α-Linolenic Acid and Its Mode of Action through the Inhibition of Nitric Oxide Production and Inducible Nitric Oxide Synthase Gene Expression via NF-κB and Mitogen-Activated Protein Kinase Pathways," J. Agric. Food Chem., vol. 55, 2007, pp. 5073-5080.

Shapiro, "Matrix metalloproteinase degradation of extracellular matrix: biological consequences," Current Opinion in Cell Biology, vol. 10, 1998, pp. 602-608.

Stern et al., "Hyaluronan in skin: aspects of aging and its pharmacologic modulation," Clinics in Dermatology, vol. 26, 2008, pp. 106-122.

Vandesompele et al., "Accurate normalization of real-time quantitative RT-PCR data by geometric averaging of multiple internal control genes," Genome Biology, vol. 3, No. 7, Jun. 18, 2002, pp. 1-12.

English Translation of Monpoint et al., "Essential Fatty Acids in Dermatology", Ann. Dermatol. Venereol., vol. 119, 1992, pp. 1-7.

English Translation of FR 2580644, pp. 1-46, (1986).

* cited by examiner

UNSATURATED FATTY ACID MONOESTERS AND DIESTERS ON ASCORBIC ACID AND COSMETIC USES THEREOF

The present invention concerns derivatives of ascorbic acid and pharmaceutical or cosmetic compositions containing the same, their method of preparation and the uses thereof in particular as medication or as active cosmetic ingredient.

Ascorbic acid is an organic acid having antioxidant properties. The natural sources of ascorbic acid are fresh fruit and vegetables, in particular citrus fruits.

On account of its antioxidant properties, ascorbic acid is often used in the agri-food industry as preservative under code number E300 in the list of food additives. Ascorbic acid is also used in the cosmetic industry for its known anti-radical and keratolytic properties.

Ascorbic acid is in the form of a white powder which easily becomes colored in air or in the presence of humidity.

Unsaturated fatty acids correspond to fatty acids having one or more unsaturations.

The term mono-unsaturated fatty acid is used when they comprise a single unsaturation. The term polyunsaturated fatty acid is used when they comprise several unsaturations.

Unsaturated fatty acids may also be of plant origin.

Unsaturated fatty acids are divided into different classes. These classes are defined by the position of the first unsaturation starting from the side opposite the acid group.

In particular, a distinction is made between three main classes of unsaturated fatty acids: omega 3, omega 6 and omega 9. The cis unsaturated fatty acids of the omega 3, omega 6 and omega 9 series comprise several so-called essential fatty acids. These fatty acids are said to be essential since they can only be provided via food intake.

The omega 9 mono-unsaturated fatty acids whose main constituent is oleic acid (C18:1) are known to have beneficial effects on the prevention of cardiovascular disease.

The polyunsaturated fatty acids (PUFAs) belonging to the omega 3 and omega 6 class are also known to have preventive effects against cardiovascular disease and cancer. It is particularly recommended by the French food safety agency AFSSAP to observe a ratio between omega 3 and omega 6 unsaturated fatty acids in food, namely a ratio of one alpha linolenic acid per 5 linoleic acids.

In addition to their metabolic effects, they are capable of modifying the expression of genes encoding intracellular proteins. These gene effects of PUFAs appear to operate via nuclear receptors called PPARs (peroxysome proliferator activated receptor). PPARs belong to the family of hormonal nuclear receptors of steroid type. They form heterodimers with the RxR receptors (RetinoicxReceptor) of retinoic acid and modulate gene expression. Therefore the ω3 PUFAs appear to be negative regulators of inflammatory response, inhibiting the NF-KB activation pathway via the inducing of the expression of IKBα the major inhibitor of the NF-KB pathway (Ren J and Chung SH. *J Agric Food Chem.* 2007 55: 5073-80). In addition, the ω3 PUFAs have inhibiting action on the synthesis of arachidonic acid to the benefit of the synthesis of docosahexanoic and eicosapentanoic acids (Calder P C. Lipids: 2001: 36, 1007-24).

Unsaturated fatty acids, in particular polyunsaturated fatty acids, are known for their dermatological properties (Monpoint S, Guillot B, Truchetet F et al. Essential fatty acids in dermatology. *Ann Dermatol Venereol*, 1992, 119: 233-239). In particular linoleic acid is a polyunsaturated fatty acid involved in the manufacture of the cell membrane. A deficiency in linoleic acid leads to dryness of the skin and the presence of allergy.

Figure 1:
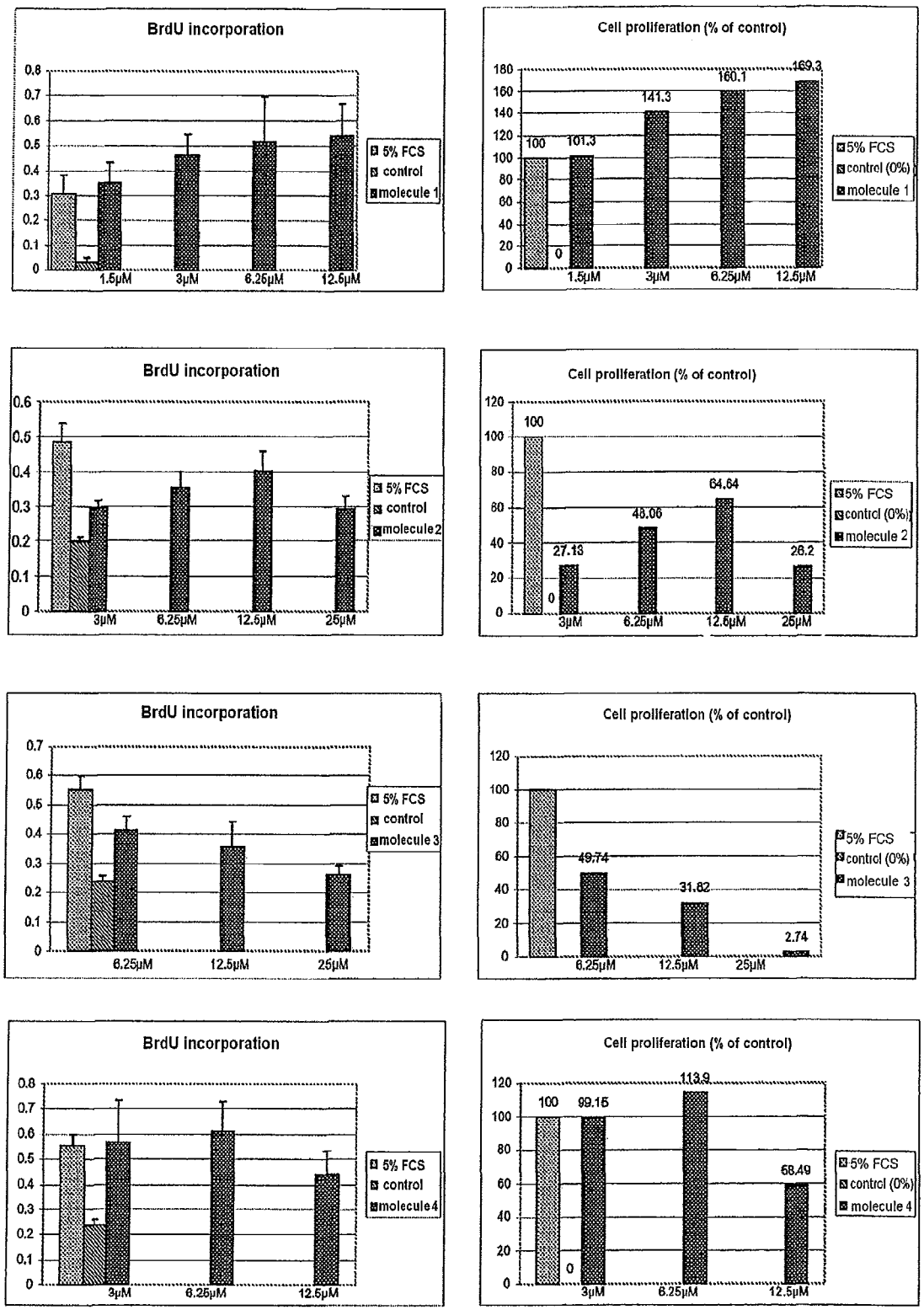
FIG. 1 shows increase in BrdU incorporation in the left column and stimulated cellular proliferation of cells in the right column.

The compounds of the invention are diesters or monoesters of unsaturated fatty acid on ascorbic acid whose hydroxyls at position 5 and 6 are protected by a cyclic acetal and more particularly a cyclic acetal of acetone (acetonide). This function is easily hydrolysable in a slightly acid medium, namely on the skin which has an acid pH of between 5.2 and 7. The cyclic acetal will therefore protect the ascorbic acid against oxidation of its side chain. The use of a cyclic acetal allows a structure to be obtained of acceptable size having strong solubility in fatty phases.

The esters of fatty acids can also be easily cleaved by the esterases present in the skin, which allows the release of unsaturated fatty acids (Redoules, D., Tarroux, R., Assalit, M. F. and Perié, J. J. Characterization and assay of five enzymatic activities in the stratum corneum using tape-stripping, *Skin Pharmacol. Appl. Skin Physiol.,* 12, 182-192 (1999)). The cleaving of the esters of unsaturated fatty acids by the esterases present in the skin therefore allows the slow diffusion of active ingredients, which corresponds to the concept of drug delivery.

For the compounds of formula (I) according to the present invention, the action of the skin esterases on the ester bonds leads to the release of one unsaturated fatty acid and of one molecule of ascorbic acid when a mono-ester of unsaturated fatty acid is used; or of two unsaturated fatty acids and of one molecule of ascorbic acid via the mono-ester at position 2 when a diester of unsaturated fatty acid is used.

In particular for diesters of unsaturated fatty acids, the action of the esterases will firstly lead to the formation of a mono-ester of an unsaturated fatty acid and to the release of ascorbic acid, then to the release of ascorbic acid and of another unsaturated fatty acid (Scheme 1).

Scheme 1: Example of a cleavage reaction by skin esterases

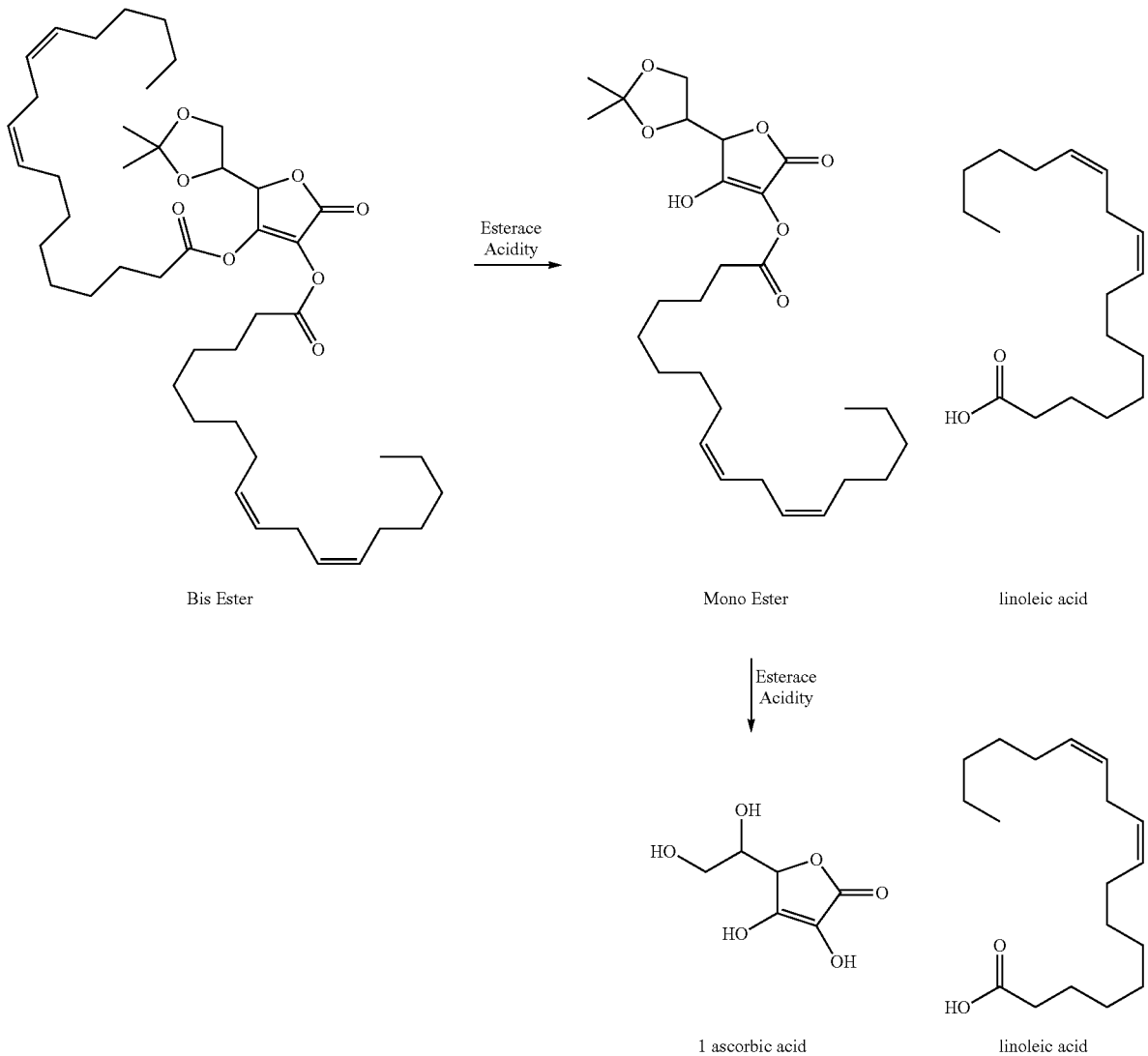

Bis Ester → Mono Ester + linoleic acid → l ascorbic acid + linoleic acid

Therefore the subject of the present invention is a compound of following general formula (I):

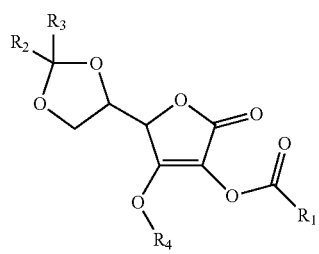

in which $R_1$ is a hydrocarbon chain derived from a $C_{12}$ to $C_{24}$ unsaturated fatty acid comprising at least one unsaturation, advantageously 1 to 6 and preferably 1 to 4; and $R_2$ and $R_3$ are independently or simultaneously: a hydrogen or $C_1$-$C_3$ alkyl or a Phenyl; and $R_4$ is a hydrogen atom or $COR_1'$, where $R_1'$ is a hydrocarbon chain derived from a $C_{12}$ to $C_{24}$ unsaturated fatty acid comprising at least one unsaturation, advantageously 1 to 6 and preferably 1 to 4.

By "unsaturation" in the meaning of the invention is meant a double bond C=C.

By "unsaturated fatty acid" in the meaning of the present invention is meant a straight-chain carboxylic acid ($R_1CO_2H$) or ($R_1'CO_2H$) acid comprising between 12 and 24 carbon atoms, preferably 14 to 18 carbon atoms, more preferably 18 carbon atoms (including the carbon atom of the carboxylic acid function) and comprising at least one C=C double bond, preferably 1 to 4 C=C double bonds, these double bonds preferably having a cis configuration.

By "hydrocarbon chain of an unsaturated fatty acid" in the meaning of the present invention is meant the hydrocarbon chains ($R_1$) or $R_1'$) linked to the acid function of the unsaturated fatty acid ($R_1CO_2H$) or ($R_1'CO_2H$). $R_1$ and $R_1'$ therefore represent a straight hydrocarbon chain comprising 11 to 23, preferably 13 to 17 and further preferably 17 carbon atoms and comprising at least one, preferably 1 to 4, C=C double bonds, these double bonds preferably having a cis configuration. According to the invention, if $R_4$ represents $COR_1'$, $R_1$ and $R_1'$ may be the same or different.

The unsaturated fatty acids may be lauroleic acid ($C_{12:1}$), myristoleic acid ($C_{14:1}$), palmitoleic acid ($C_{16:1}$), oleic acid ($C_{18:1}$), ricinoleic acid ($C_{18:1}$); gadoleic acid ($C_{20:1}$), erucic acid ($C_{22:1}$), α-linolenic acid ($C_{18:3}$); stearidonic acid ($C_{18:4}$), eicosatrienoic acid ($C_{20:3}$), eicosatetraenoic acid ($C_{20:4}$), eicosapentaenoic acid ($C_{20:5}$), docosapentaenoic acid ($C_{22:5}$), docosahexaenoic acid ($C_{22:6}$), tetracosapentaenoic acid ($C_{24:5}$), tetracosahexaenoic acid ($C_{24:6}$), linoleic acid ($C_{18:2}$), gamma-linolenic acid ($C_{18:3}$), eicosadienoic acid ($C_{20:2}$); dihomo-gamma-linolenic acid ($C_{20:3}$), arachidonic acid ($C_{20:4}$), docosatetraenoic acid ($C_{22:2}$), docosapentaenoic acid ($C_{22:5}$), adrenic acid ($C_{22:4}$) and calendic acid ($C_{18:3}$).

Advantageously, the compounds of the invention are those for which $R_1$ is an unsaturated fatty acid chosen from the group composed of oleic acid ($C_{18:1}$), linoleic acid ($C_{18:2}$), α-linolenic acid ($C_{18:3}$) and γ-linolenic acid ($C_{18:3}$).

Advantageously, the compounds of the invention are those in which, when $R_4$ represents $COR_1'$, $R_1'$ is an unsaturated fatty acid chosen from among the group comprising oleic acid ($C_{18:1}$), linoleic acid ($C_{18:2}$), α-linolenic acid ($C_{18:3}$) and γ-linolenic acid ($C_{18:3}$).

By "alkyl" in the meaning of the present invention is meant straight or branched, saturated aliphatic hydrocarbon chains and comprising the specified number of carbon atoms. Mention may be made for example of methyl, ethyl and propyl.

Advantageously, the compounds of the invention are those for which $R_2$ and $R_3$ represent a $C_1$-$C_3$ alkyl.

Advantageously, the compounds of the invention are those for which $R_2$ and $R_3$ represent a methyl.

Advantageously, the compounds of the invention are those for which $R_1$ represents the hydrocarbon chain of a $C_{14}$ to $C_{18}$ unsaturated fatty acid comprising 1 to 3 unsaturations.

Advantageously the compounds of the invention are those for which, when $R_4$ represents $COR_1'$, $R_1'$ represents the hydrocarbon chain of a $C_{14}$ to $C_{18}$ unsaturated fatty acid comprising 1 to 3 unsaturations.

According to one embodiment of the invention, the formula (I) compounds are those for which $R_4$ represents $COR_1'$.

According to another embodiment of the invention, the formula (I) compounds are those for which $R_4$ represents a hydrogen atom.

In particular, the compounds of the invention can be chosen from among the following molecules:

1. Molecule of General Formula (I) where $R_4$ Represents $COR_1'$
   dioctadeca-9,12-dienoate of (9Z,9'Z,12Z,12'Z)-2-(2,2-dimethyl-1,3-dioxolan-4-yl)-5-oxo-2,5-dihydrofuran-3,4-diyl
   dioctadeca-9,12,15-trienoate of (9Z,9'Z,12Z,12'Z,15Z,15'Z)-2-(2,2-dimethyl-1,3-dioxolan-4-yl)-5-oxo-2,5-dihydrofuran-3,4-diyl,
   dioctadeca-6,9,12-trienoate of (6Z,6'Z,9Z,9'Z,12Z,12'Z)-2-(2,2-dimethyl-1,3-dioxolan-4-yl)-5-oxo-2,5-dihydrofuran-3,4-diyl
   dioleate of (Z)-2-(2,2-dimethyl-1,3-dioxolan-4-yl)-5-oxo-2,5-dihydrofuran-3,4-diyl.

2. Molecule of General Formula (I) where $R_4$ Represents a Hydrogen Atom
   (9Z,12Z)-5-(2,2-dimethyl-1,3-dioxolan-4-yl)-4-hydroxy-2-oxo-2,5-dihydrofuran-3-yl octadeca-9,12-dienoate
   (9Z,12Z,15Z)-5-(2,2-dimethyl-1,3-dioxolan-4-yl)-4-hydroxy-2-oxo-2,5-dihydrofuran-3-yl octadeca-9,12,15-trienoate
   (6Z,9Z,12Z)-5-(2,2-dimethyl-1,3-dioxolan-4-yl)-4-hydroxy-2-oxo-2,5-dihydrofuran-3-yl octadeca-6,9,12-trienoate
   5-(2,2-dimethyl-1,3-dioxolan-4-yl)-4-hydroxy-2-oxo-2,5-dihydrofuran-3-yl oleate.

A further subject of the present invention is a compound of general formula (I) for use thereof as medication.

A further subject of the present invention is a compound of general formula (I) for use thereof as cosmetic active ingredient.

In particular, a further subject of the invention is a compound of general formula (I) for use thereof as depigmenting active ingredient, anti-age active ingredient, antioxidant active ingredient, hydrating active ingredient, anti-inflammatory active ingredient, or as active ingredient for stimulating body and/or head hair re-growth.

The invention also extends to a pharmaceutical or cosmetic composition characterized in that it comprises at least one compound of general formula (I) in combination with a pharmaceutically or cosmetically acceptable excipient particularly adapted for transcutaneous administration.

In the present invention by "pharmaceutically or cosmetically acceptable" is meant useful in the preparation of a pharmaceutical or cosmetic composition which is generally safe, non-toxic and neither biologically nor otherwise undesirable and which is acceptable for a therapeutic or cosmetic use notably via topical application.

The pharmaceutical or cosmetic compositions of the invention may be in forms which are usually known for topical administration to the skin or scalp i.e. in particular lotions, foams, gels, dispersions, emulsions, shampoos, sprays, serums, masks, body milks or creams, with excipients particularly allowing penetration into the skin in order to improve the properties and accessibility of the active ingredient. The pharmaceutical or cosmetic compositions of the invention may also be in the form of gels for injection (in combination for example with hyaluronic acid, collagen or alginate . . . ) usually used as wrinkle fillers.

These compositions, in addition to the compound(s) of the present invention, generally contain a physiologically acceptable medium in general water or solvent based, e.g. alcohols, ethers or glycols. They may also contain surfactant agents, complexing agents, preserving agents, stabilizing agents, emulsifiers, thickeners, gelling agents, humectants, emollients, trace elements, essential oils, fragrances, coloring agents, matifying agents, chemical or mineral filters, hydrating agents or spa waters, etc.

These compositions may also contain other active ingredients leading to a complementary or optionally synergic effect.

Advantageously the compositions of the present invention comprise from 0.01% to 10% by weight, preferably 0.1% to 5% by weight of the compound(s) of general formula (I).

These compositions are more particularly intended for depigmenting the skin and/or head hair and/or body hair, for the treatment and/or prevention of skin ageing, for hydrating the epidermis, stimulating the re-growth of head and/or body hair, or for treating inflammation of the sin.

A further subject of the present invention is a cosmetic method for treating and/or preventing skin ageing.

The subject of the invention also extends to a method for whitening and lightening human skin and/or body hair and/or head hair by applying a cosmetic composition containing at least one compound of general formula (I)

A further subject of the invention concerns a method for preparing a formula (I) compound by coupling an unsaturated fatty acid, whose carboxylic function is in activated form, with a derivative of ascorbic acid of formula (II).

Scheme 2: Method for preparing a compound of formula (I)

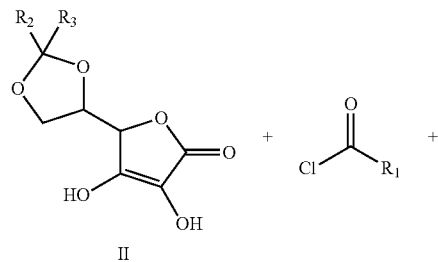

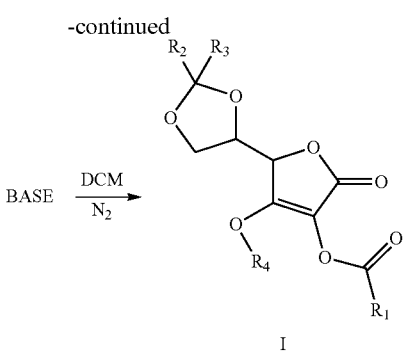

(DCM=dichloromethane)
(where $R_4$ may represent $COR_1'$ or a hydrogen atom)

The coupling reaction of the invention is conducted in the presence of a base and optionally in the presence of a coupling auxiliary.

The base may be pyridine for example or triethylamine.

The coupling auxiliary may for example be 4-dimethylaminopyridine.

By "activated form" in the meaning of the present invention is meant a carboxylic acid function modified to make it more active with respect to nucleophiles. These activated forms are well known to the person skilled in the art and may in particular be an acid chloride.

The present invention will be better understood in the light of the following non-limiting examples.

EXAMPLE (1)

Synthesis of the Compounds of the Invention

Molecule of General Formula (I) where $R_4$ Represents $COR_1'$:

1.1 General Method A: Starting from a Chloride of an Unsaturated Fatty Acid and Pyridine 1.1a Molecule 1: diactodeca-9,12-dienoate of (9Z,9'Z,12Z,12'Z)-2-(2,2-dimethyl-1,3-dioxolan-4-yl)-5-oxo-2,5-dihydrofuran-3,4-diyl

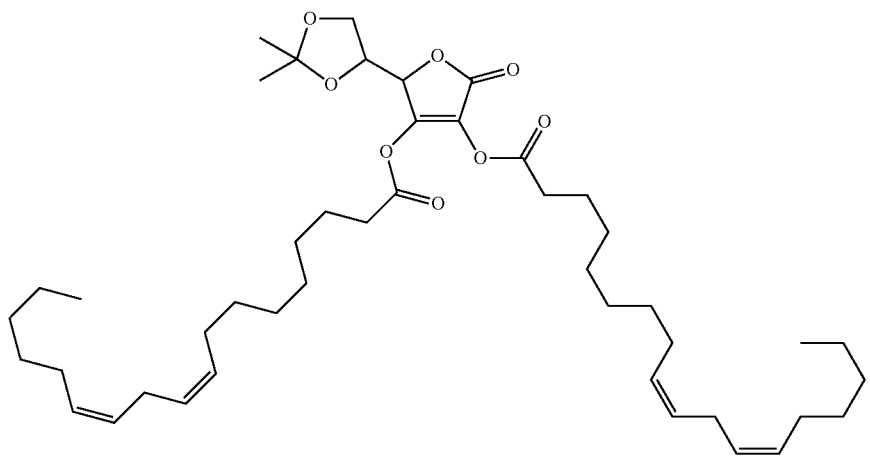 [SMILES: CCCCC/C=C\C/C=C\CCCCCCCC(=O)OC1=C(OC(=O)CCCCCCC/C=C\C/C=C\CCCCC)C(C2COC(C)(C)O2)OC1=O]

Pathway 1: To a solution of 5,6-O-Isopropylidene-ascorbic acid (1.08 g, 5 mmol, 1 eq.) and 4-Dimethylaminopyridine (61 mg, 0.5 mmol, 0.1 eq.) in 10 ml of anhydrous pyridine and under nitrogen, are added 2.9 g of linoleoyl chloride (10 mmol, 2 eq.) then the mixture is left under agitation at ambient temperature for 16 hours. The reaction is followed by thin layer chromatography (TLC).

After return to ambient temperature, the solvent is evaporated then the residue extracted with an ether/water mixture. The organic phase is washed twice with 1N HCl solution then with NaCl-saturated solution. After drying over magnesium sulfate an oil is obtained after evaporation of the solvent.

The residue is then purified on silica with the heptane/ethyl acetate mixture (100:0 to 70:30) or by preparative HPLC. The product obtained in the form of a colorless oil is dried in vacuo overnight.

1.49 g are obtained with a yield of 40%.

$^1$H NMR (400 MHz, CDCl$_3$): δ: 0.83 (2t, 6H); 1.27-1.39 (m, 34H); 1.68 (m, 4H); 2.06 (m, 8H); 2.53 (2t, 4H); 2.77 (2t, 4H); 4.01 (dd, 1H); 4.18 (dd, 1H); 4.35 (td, 1H); 5.14 (d, 1H); 5.35 (m, 8H).

$^{13}$C NMR (100 MHz, CDCl$_3$): δ: 14.01; 22.6-33.6 (aliphatic); 65.19; 72.9; 75.3; 76.7; 77; 110.8; 122.0; 127-130; 150.8; 167.7; 168, 169.

Pathway 2: 5,6-O-Isopropylidene-ascorbic acid (1 g) is placed in suspension in dichloromethane (19 ml). Pyridine (0.79 ml) is added and the reaction medium becomes heterogeneously white (T=15° C.). After 10 minutes under agitation, the reaction medium is cooled to 0° C. using an ice bath. A solution of linoleoyl chloride (2.98 ml) in dichloromethane (6 ml) is added over a period of 5 minutes after which the ice bath is removed and the reaction medium is left under agitation 30 minutes.

The reaction medium is washed with water (3×50 ml) with a 2% copper sulfate solution (w/v) (2×50 ml) then again with water (50 ml). The organic phase is dried over magnesium sulfate then concentrated in vacuo to afford a brown-colored oil (3.3 g; Yield 96%).

This oil is stored in a nitrogen atmosphere at −18° C.

1.2 General Method B: Starting from an Unsaturated Fatty Acid Chloride and Triethylamine 1.2a Molecule 2: dioctadeca-9,12,15-trienoate of (9Z,9'Z,12Z,12'Z,15Z,15'Z)-2-(2,2-dimethyl-1,3-dioxolan-4-yl)-5-oxo-2,5-dihydrofuran-3,4-diyl

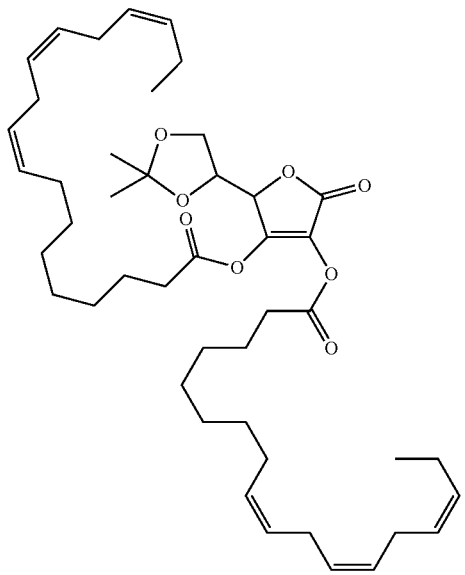 [SMILES: CC/C=C\C/C=C\C/C=C\CCCCCCCC(=O)OC1=C(OC(=O)CCCCCCC/C=C\C/C=C\C/C=C\CC)C(C2COC(C)(C)O2)OC1=O]

To a solution of 5,6-O-Isopropylidene-ascorbic acid (432 mg, 2 mmol, 1 eq.) and triethylamine (960 µl, 7 mmol, 3.5 eq.) in 20 ml of anhydrous dichloromethane and under nitrogen, are added 1.91 ml of linolenoyl chloride (6 mmol, 3 eq., 70%, technical), then the mixture is left under agitation at ambient temperature for 16 hours. The reaction is followed by TLC.

After return to ambient temperature, the solvent is evaporated and the residue extracted with an ether/water mixture. The organic phase is washed twice with 1N HCl solution then with NaCl-saturated solution. After drying over magnesium sulfate, an oil is obtained after evaporation of the solvent. The residue is then purified on silica with the heptanes/ethyl acetate mixture (100:0 to 70:30) or by preparative HPLC. The product obtained in the form of a colorless oil is dried in vacuo overnight.

604 mg are obtained with a yield of 41%.

$^1$H NMR (400 MHz, CDCl$_3$): δ: 0.91 (2t, 6H); 1.27-1.39 (m, 30H); 1.67 (m, 4H); 2.06 (m, 4H); 2.53 (2t, 4H); 2.79 (2t, 4H); 4.09 (dd, 1H); 4.18 (dd, 1H); 4.36 (td, 1H); 5.14 (d, 1H); 5.38 (m, 12H).

1.2b Molecule 3: dioctadeca-6,9,12-trienoate of (6Z,6'Z,9Z,9'Z,12Z,12'Z)-2-(2,2-dimethyl-1,3-dioxolan-4-yl)-5-oxo-2,5-dihydrofuran-3,4-diyl

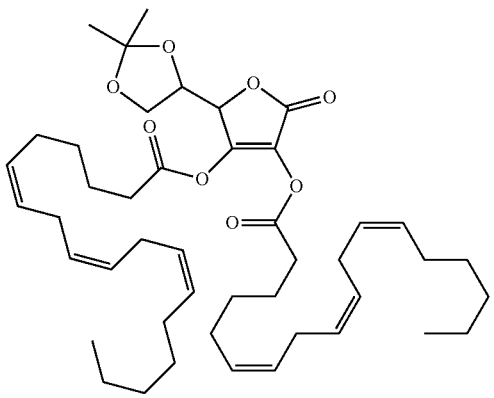 [SMILES: CCCCC/C=C\C/C=C\C/C=C\CCCCC(=O)OC1=C(OC(=O)CCCC/C=C\C/C=C\C/C=C\CCCCC)C(C2COC(C)(C)O2)OC1=O]

Starting from 2.5 equivalents of gamma linolenoyl chloride (98%).

Colorless oil with a yield of 68%.

$^1$H NMR (400 MHz, CDCl$_3$): δ: 0.89 (2t, 6H); 1.27-1.44 (m, 20H); 1.47 (m, 4H); 1.68 (m, 4H); 2.06 (m, 8H); 2.55 (m, 4H); 2.80 (m, 8H); 4.01 (dd, 1H); 4.18 (dd, 1H); 4.36 (td, 1H); 5.14 (d, 1H); 5.37 (m, 12H).

1.2.c Molecule 4 dioleate of (Z)-2-(2,2-dimethyl-1,3-dioxolan-4-yl)-5-oxo-2,5-dihydrofuran-3,4-diyl

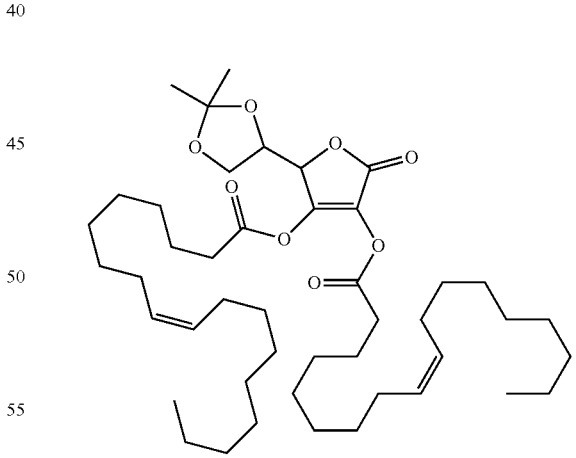

Starting from 2.5 equivalents of oleoyl chloride (98%).

Colorless oil with a yield of 53% after purification.

$^1$H NMR (400 MHz, CDCl$_3$): δ: 0.88 (2t, 6H) ; 1.26-1.55 (m, 46H); 1.67 (m, 4H); 2.00 (m, 8H); 2.53 (m, 4H); 2.77 (2t, 4H); 4.09 (dd, 1H); 4.18 (dd, 1H); 4.36 (td, 1H); 5.14 (d, 1H); 5.34 (m, 4H).

EXAMPLE (2)

Synthesis of the Compounds of the Invention

Molecule of General Formula (I) where $R_4$ Represents a Hydrogen Atom 2.1 Molecule 5 (9Z,12Z)-5-(2,2-dimethyl-1,3-dioxolan-4-yl)-4-hydroxy-2-oxo-2,5-dihydrofuran-3-yl octadeca-9,12-dienoate

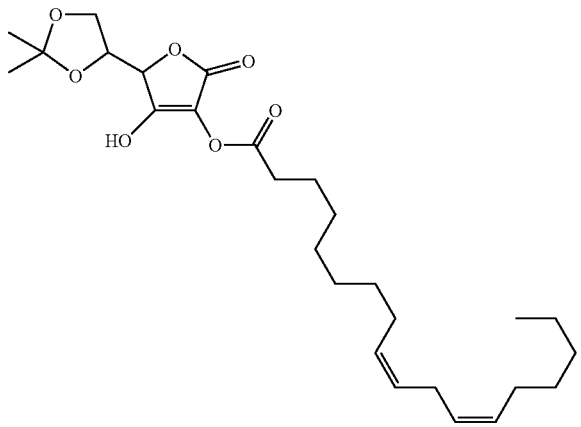

In a three-necked flask under nitrogen a suspension is prepared of 5,6-O-Isopropylidene-ascorbic acid (5.5 g; 25.44 mmol) in 110 ml acetone after which 3.53 ml of triethylamine are added. Formation of an abundant white precipitate. Linoleoyl chloride (3.55 ml; 11.06 mmol) is then added dropwise over 3 minutes and the mixture then left under agitation 10 minutes at ambient temperature. The mixture again becomes limpid and then a small precipitate of triethylammonium chloride is formed. The solid is filtered through a sintered filter and the filtrate drawn up to obtain an oil. This oil is dissolved in 100 ml of ethyl acetate and washed 3 times with saturated NaCl solution. The organic phase is dried over magnesium sulfate, filtered and evaporated to arrive at 4.76 g of a brown solid giving a yield of 90%.

$^1$H NMR (300 MHz, CDCl$_3$): δ: 0.90 (t,3H); 1.27-1.39 (m, 20H); 1.70 (m, 2H); 2.06 (m, 4H); 2.58 (t, 2H); 2.78 (t, 2H); 4.13 (dd, 1H); 4.20 (dd, 1H); 4.43 (m, 1H); 4.65 (d, 1H); 5.37 (m, 4H).

[M+Na]$^+$=501.2; [2M+Na]$^+$=979.7
[M−H]$^−$=477.3; [2M−H]$^−$=955.7

2.2 Molecule 6 5-(2,2-dimethyl-1,3-dioxolan-4-yl)-4-hydroxy-2-oxo-2,5-dihydrofuran-3-yl oleate Same operating mode as for molecule 5 starting from oleoyl chloride.

White solid, Yield: 96%;

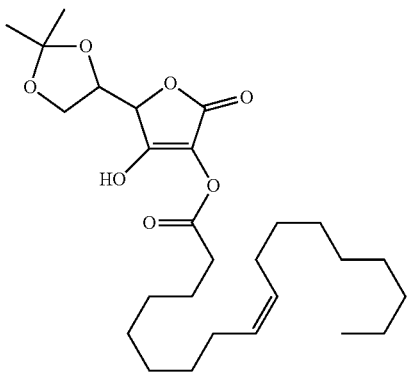 [SMILES: CCCCCCCC/C=C\CCCCCCCC(=O)OC1=C(O)C(C2COC(C)(C)O2)OC1=O]

$^1$H NMR (300 MHz, CDCl$_3$): δ: 0.89 (t, 3H); 1.28-1.42 (m, 26H); 1.69 (m, 2H); 2.02 (m, 4H); 2.62 (m, 2H); 4.15 (dd, 1H); 4.22 (dd, 1H); 4.45 (td, 1H); 4.70 (d, 1H); 5.36 (m, 2H).

[M+Na]$^+$=503.2
[M−H]$^−$=479.3

2.3 Molecule 7 (9Z,12Z,15Z)-5-(2,2-dimethyl-1,3-dioxolan-4-yl)-4-hydroxy-2-oxo-2,5-dihydrofuran-3-yl ocatdeca-9,12,15-trienoate Same operating mode as for molecule 5 starting from linolenoyl chloride.

Brown solid. Yield: 91%.

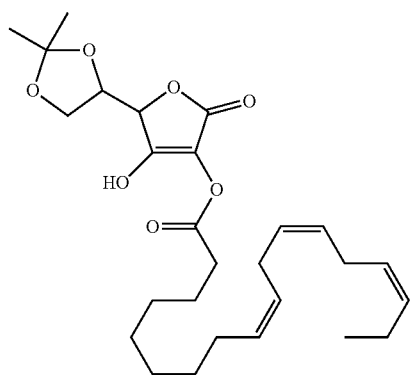 [SMILES: CC/C=C\C/C=C\C/C=C\CCCCCCCC(=O)OC1=C(O)C(C2COC(C)(C)O2)OC1=O]

$^1$H NMR (300 MHz, CDCl$_3$): δ: 0.99 (t, 3H); 1.30-1.42 (m, 14H); 1.72 (m, 2H); 2.08 (m, 4H); 2.62 (m, 2H); 2.82 (m, 4H); 4.15 (dd, 1H); 4.22 (dd, 1H); 4.45 (td, 1H); 4.70 (d, 1H); 5.38 (m, 6H).

[M+Na]$^+$=499.1
[M+H]$^+$=477.2

EXAMPLE (3)

Composition According to the Invention

1. A Cream

| Ingredients (trade names) | INCI name | Percentage | Function |
|---|---|---|---|
| Purified water | Water | QS* to 100% | |
| Glycerin | Glycerin | 3 | Humectant |
| EDTA**, 2Na | Disodium EDTA | 0.1 | Complexing agent |
| Phenoxyethanol | Phenoxyethanol | 0.35 | Preserving agent |
| Sepiplus ™ 400 | Polyacrylate-13 and Polyisobutene and Polysorbate 20 and water | 1 | Gelling and stabilizing agent |
| Simulsol ™ 165 | Glyceryl stearate and PEG stearate *** 100 | 4 | Emulsifying agent |
| Lanette ® 16 | Cetyl alcohol | 1 | Consistency factor |
| Myritol ® 318 | Capric/caprylic triglycerides | 6 | Emollient |
| Primol ® 352 | Liquid paraffin | 4 | Emollient |
| Cetiol ® CC | Dicaprylyl carbonate | 4 | Emollient |

-continued

| Ingredients (trade names) | INCI name | Percentage | Function |
|---|---|---|---|
| Molecule 1 | 9Z, 9'Z, 12Z, 12'Z)-2-(2,2-dimethyl-1,3-dioxolan-4-yl)-5-oxo-2,5-dihydrofuran-3,4-diyl dioctadeca-9, 12-dienoate | 0.5 | Active ingredient |
| Chlorphenesin | Chlorphenesin | 0.27 | Preserving agent |
| Micropearl M100 | Methyl polymethacrylate | 1 | Powder |
| Fragrance | Fragrance | 0.1 | Fragrance |

QS: quantum satis
*EDTA: ethylenediaminetetraacetic acid
***PEG: polyethylene glycol 2. A Milk

| Ingredients (trade names) | INCI name | Percentage | Function |
|---|---|---|---|
| Purified water | Water | QS to 100% | |
| Glycerin | Glycerin | 3 | Humectant |
| EDTA**, 2Na | Disodium EDTA | 0.1 | Complexing agent |
| Phenoxyethanol | Phenoxyethanol | 0.35 | Preserving agent |
| Synthalen ® K | Carbomer | 0.2 | Gelling and stabilizing agent |
| Pemulen ® TR1 | a copolymer of acrylic acid and alkyl methacrylate | 0.3 | Gelling and stabilizing agent |
| Myritol ® 318 | Capric/caprylic triglyceride | 4 | Emollient |
| Primol ® 352 | Liquid paraffin | 4 | Emollient |
| Molecule 1 | (9Z, 9'Z, 12Z, 12'Z)-2-(2,2-dimethyl-1,3-dioxolan-4-yl)-5-oxo-2,5-dihydrofuran-3,4-diyl dioctadeca-9,12-dienoate | 0.5 | Active ingredient |
| Chlorphenesin | Chlorphenesin | 0.27 | Preserving agent |
| Fragrance | Fragrance | 0.1 | Fragrance |

QS: quantum satis
**EDTA: ethylenediaminetetraacetic acid

EXAMPLE (4)

Results of Biological Tests 4.1 Targets of Biological Tests

The extracellular matrix (ECM) is a dynamic structure having a structural, regulatory role for tissues. The ECM of the dermis is formed of fibers (collagen and elastin) and of fundamental substance (water, mineral salts, glycoproteins, hyaluronic acid and proteoglycans). It imparts to the skin its turgescence and mechanical properties: firmness, elasticity and tonicity. The ECM permanently undergoes rearrangement in relation to the equilibrium between the synthesis and degradation of its constituent macromolecules. The ECM is formed of four types of macromolecules: collagen, elastin, structural glycoproteins and glycosaminoglycans (such as hyaluronic acid).

Collagens are fibrous proteins that are highly abundant in the dermis. In majority they are fibrillar collagens of type I, III and V. Collagens form the essential component of the fibrous network and play a mechanical role imparting resistance and elasticity to the skin.

The degradation of the ECM sets in over the course of some physiological processes (scar healing, embryonic development, angiogenesis . . . ) but also during pathological processes (arthritis, arthrosis, atherosclerosis, tumor development and formation of metastases . . . ) (Fisher et al., *N. Engl. J. Med.* 333: 1419, 1997; Shapiro S D *Current Opinion in Cell Biology* 10: 602, 1998). The components of the ECM are mostly degraded by enzymes of endopeptidase type called matrix metalloproteinases or MMPs (Nagase and Woessner, *J. Biol. Chem.* 274: 21491, 1999). MMPs take an active part in the scar healing process but they also contribute to skin slackening and the onset of wrinkles. MMPs are enzymes of zinc endopeptidase type.

MMP-1, or interstitial collagenase, mostly degrades the triple helix of type I fibrillar collagens, and also degrades collagens II, II, VIII and X (Kähari V M and Saarialho-Kere U, *Exp. Dermatol.* 6: 199, 1997). MMP-1 therefore plays a crucial role in the initiation of the degradation of collagens. This collagenolytic activity is also associated with scar healing. Type 1 stromelysin (MMP-3) degrades glycoproteins such as fibronectin and laminin, some proteoglycans, elastin, gelatin and collagens IV et V. At skin level, MMP-1s and MMP-3s are expressed both by the keratinocytes and by the fibroblasts. During skin ageing, a reduction in the quantity of hyaluronic acid is also observed both at epidermal and at dermal level. This reduction is the result of a decrease in the synthesis of hyaluronic acid and an increase in hyaluronidase activity (Stern R, Maibach H I (2008) Hyaluronan in skin: aspects of aging and its pharmacologic modulation. Clin Dermatol 26: 22).

In addition, numerous studies evidence an increase in pro-inflammatory cytokines (IL-6, IL-8 . . . ) during aging (Franceschi et al, *Mechanisms of ageing and development*, 92, 2006). This pro-inflammatory context or "inflammaging" appears to be directly involved in the onset of some signs of ageing, in particular at skin level (Mocchegiani et al., *Biomed Central*, 1:5, 2004; Licastro et al., *Neurobiol. Aging*, 2006). The interleukins, cytokines produced by the T lymphocytes, are then expressed (IL-6 or IL-8).

To evidence the activity of the compounds of general formula (I) against skin ageing and against inflammation, the effect of these compounds was measured on the gene expression of MMP-1, MMP-3 and IL8 in human dermal fibroblasts treated with $H_2O_2$, thereby mimicking the process of cellular senescence. The effect of these compounds of general formula (I) was also measured on the synthesis of hyaluronic acid and on hyaluronidase activity. The stimulation of the synthesis of hyaluronic acid also allows skin hydration to be improved and/or restored (Bissett D L. J. Cosmet. Dermatol. 2006 Dec. 5(4): 309-15. Glucosamine: an ingredient with skin and other benefits).

Similarly, to evidence the depigmenting activity of the compounds of general formula (I) according to the invention, the effect of these compounds was measured on the synthesis of melanin by colorimetric assay on a cell line of murine melanomas: line B16-F10.

In addition, the effect of the compounds of general formula (I) on the re-growth of head and/or body hair was also evaluated by measuring their activity on stimulation of the proliferation of dermal papilla cells and stimulation of the growth of the human hair follicle.

4.2.1. Test Protocol for the Gene Expression of MMP-1, MMP-3 and IL8 in Human Fibroblasts Cell Treatment Human dermal fibroblasts (isolated from discarded operative skin) were cultured in DMEM culture medium+10% FCS. The cells were pre-treated with vitamin C and the compound to be tested for 16 h at 37° C. and then stimulated with $H_2O_2$. The cells were then replaced in DMEM with vitamin C and dioctadeca-9,12-dienoate of (9Z,9'Z,12Z,12'Z)-2-(2,2-dimethyl-1,3-dioxolan-4-yl)-5-oxo-2,5-dihydrofuran-3,4-diyl. 72 hours after ending of stress, the fibroblasts entered into senescence: the senescent fibroblasts no longer proliferate but remain metabolically active (Hayflick, *J. Invest. Dermatol.*, 73; 8-14, 1979). The cells were then lysed with the lysis buffer of the RNeasy® kit (QIAGEN).

Reverse Transcription and Real-Time PCR

The extracted RNAs were converted to complementary DNA following the indications of the Quantitect Reverse Transcription kit by Qiagen. Real-time PCR analyses were conducted using an iQ cycler fluorescence thermocycler (BIO-RAD).

The level of expression of the mRNAs coding for MMP-1, MMP-3, IL8 was analyzed using the real-time PCR technique. To normalize the level of expression of the gene of interest, the analysis strategy developed by Vandesompela et al., Genome Biol. 3: RESEARCH0034 (2002) was chosen. Using the $\Delta C_T$ values obtained during a first PCR, the algorithm of Genorm software version 3.4 (Vandesompele J et al., *Genome Biol.* 3: RESEARCH0034 2002) compares the level of stability of three reference genes under precise experimental conditions of the cell test and allows the determination of the most stable reference gene. In our model, the three tested reference genes were the following: β-actin (Human β-actin), GAPDH (Human glyceraldehyde-3-phosphate dehydrogenase) and YWHAZ (Tyrosine-3-monooxygenase, tryptopgan-5-monooxygenase activation protein zeta polypeptide).

The first step normalizes the Ct values obtained for the gene of interest in relation to the Ct values obtained for the reference gene, for each experimental condition.

The following was therefore calculated:

$$\Delta Ct = Ct_{gene\ of\ interest} - Ct_{reference\ gene}$$

These ΔCt values represent the raw non-transformed values used for statistical analysis.

The second step of the calculation determines the variation in the number of copies of the gene of interest during treatment. To do so ΔΔCt is calculated:

$$\Delta\Delta Ct = \Delta Ct_{non-treated\ NHF} - \Delta Ct_{treated\ NHF}$$

For the non-treated control, this QR is therefore equal to 1. It is then possible to calculate an induction or inhibition factor of the gene of interest compared with this control.

4.2.2 Results of the Test on the Expression of MMP-1, MMP-3 and IL8 in Human Fibroblasts Statistical Analysis Statistical analysis was performed using a test called "one-way ANOVA". Variance analysis using the Dunnett test then allows the comparing, for each of the analyzed genes, of the ΔCt values of normal adult fibroblasts with the compounds in the presence of $H_2O_2$ in both cases. This test then gives the "p value" characterizing the significance of the results obtained for both conditions The degree of significance was established as follows:

significant for p<0.05(*)
very significant for p<0.005(**)
highly significant for p<0.001(***)
non-significant for p>0.05.

Analysis of the expression of the mRNAs of MMP-1, MMP-3 and IL-8 in senescent human dermal fibroblasts treated or non-treated with the compounds of the invention Analysis of the Relative Quantity of mRNAs The human dermal fibroblasts were incubated in the presence of ascorbic acid or dioctadeca-9,12-dienoate of (9Z,9'Z,12Z,12'Z)-2-(2,2-dimethyl-1,3-dioxolan-4-yl)-5-oxo-2,5-dihydrofuran-3,4-diyl(=active ingredient 1 in Table 2) before and after being stimulated with $H_2O_2$. To analyze the effect of these extracts on the expression of mRNAs modulated by $H_2O_2$, the samples treated with the active ingredients and stimulated with $H_2O_2$ were compared with the sample stimulated solely with $H_2O_2$. For each sample, the level of expression of the mRNA of interest had to be normalized with the level of expression of the mRNA of the most stable reference gene Analysis of Percentage Activity It is also possible to calculate percentage inhibition of the level of expression of the different mRNAs by the active ingredients to be evaluated, using the formula:

$$\% \text{ inhibition} = \frac{\left(RQ^{H202+active\ ing.} - RQ^{non-treated}\right) - \left(RQ^{H202} - RQ^{non-treated}\right)}{RQ^{H202} - RQ^{non-treated}} \times 100$$

TABLE 1

Relative quantity of mRNAs of MMP-1, MMP-3 and IL-8 of young or senescent fibroblasts, and percentage inhibition of the level of mRNA expression by the tested active ingredients.

|  | RQ | % Inhibition |
|---|---|---|
| MMP-1 | | |
| $H_2O_2$ | 3.6 | |
| Ascorbic acid (3 μM) | 3.2 | 18 |
| Molecule 1 (3 μM) | 0.9 | 105*** |
| MMP-3 | | |
| $H_2O_2$ | 5.9 | |
| Ascorbic acid (3 μM) | 3.5 | 50* |
| Molecule 1 (3 μM) | 1.9 | 81*** |
| IL-8 | | |
| $H_2O_2$ | 3.1 | |
| Ascorbic acid (3 μM) | 1.2 | 92*** |
| Molecule 1 (3 μM) | 0.9 | 102*** |

Molecule 1 (dioctadeca-9,12-dienoate of (9Z,9'Z,12Z,12'Z)-2-(2,2-dimethyl-1,3-dioxolan-4-yl)-5-oxo-2,5-dihydrofuran-3,4-diyl) more substantially inhibits the expression of MMP1, MMP3 and IL-8 than ascorbic acid.

The present invention concerns the use of compounds of general formula (I) for preventing and/or treating skin ageing.

The present invention also extends to the use of compounds of formula (I) for treating inflammatory skin reactions.

4.3.1 Test Protocol for the Assay of Melanin in Molecules B16-F10

Principle:

This is a test to measure the synthesis of melanin by colorimetric assay on a cell line of murine melanomas: line B16-F10. This test allows the evaluation of the depigmenting property of active ingredients.

The B16-F10 cells were seeded onto 96-well plates in DMEM medium supplemented with FCS (fetal calf serum) and incubated 24 hours at 37° C., 5% $CO_2$. The cells were then stimulated with α-MSH (to stimulate the synthesis of melanin, the stimulation observed was about 150%) and treated 72 hours with the active ingredients to be tested. Each concentration of active ingredient was tested at least in triplicate. Total melanin followed by intracellular melanin dissolved in lysis buffer were then assayed by absorbency reading at 405 nm. The total proteins were determined in the lysate and the results are expressed in mg melanin/mg proteins. The percentage activity was calculated as follows:

$$\% \text{ activity} = \frac{\text{Control normalized mean} - \text{Treated normalized mean}}{\text{Control normalized mean}} \times 100$$

A negative value indicates an inhibition, whereas a positive value indicates induced synthesis of melanin.

4.3.2 Results of the Assay of Melanin in B16-F10 Cells

TABLE 2

Percentage inhibition of intracellular melanin and $IC_{50}$ values.

|  | 100 μM | 50 μM | 20 μM | 10 μM | IC50 μM |
|---|---|---|---|---|---|
| Vitamin C | −22 | −5 | −7 | 5 | nd* |
| Molecule 1 | −71 | −41 | −21 | −9 | 67 |
| Molecule 2 | nd | nd | −53 | −11 | 20 |
| Molecule 3 | nd | nd | −50 | −25 | 20 |
| Molecule 4 | nd | −44 | −6 | 16 | 53 |
| Molecule 5 | −78 | −35 | −13 | −4 | 66 |
| Molecule 6 | −49 | −7 | nd | nd | 105 |

*nd non-determined

The results of these tests (Table 2) show that the inhibition of the synthesis of intracellular melanin by molecules 1, 2, 3, 4, 5, 6 is greater than that of vitamin C.

The present invention also concerns the use of the compounds of general formula (I) for depigmenting the skin and/or body hair and/or head hair.

4.4.1 Assay Protocol for the Synthesis of Hyaluronic Acid

The keratinocytes HaCaT are cultured in DMEM culture medium+10% FCS. The cells are treated with the active ingredients to be tested (Table 1) for 48 h at 37° C. The synthesized hyaluronic acid (HA) is assayed in the culture medium using an ELISA type kit (Echelon®).

The percentage activity was determined as follows percentage variation compared with the control $\%p/C = ([HA]_{active\ ingred.}/[HA]_{control} \times 100) - 100$ 4.4.2 Results of the Assay of Hyaluronic Acid on the Line of Human Keratinocytes HaCaT

TABLE 3

Percentage stimulation of the synthesis of hyaluronic acid.

| Concentration | 2 μM | 20 μM | 30 μM | 300 μM |
|---|---|---|---|---|
| Vitamin C | * | * | 9 | 19 |
| Molecule 1 | 132 | 70 | * | * |

*nd non-determined

The results of these tests (Table 3) show that vitamin C, used at biologically active concentrations (30 and 300 μM) has no effect on the synthesis of hyaluronic acid in HaCaT keratinocytes.

Molecule 1, at 2 and 20 μM, strongly stimulates the synthesis of hyaluronic acid: +132%+70%.

The present invention therefore concerns the use of the compounds of general formula I for the prevention and/or treatment of skin ageing. The invention also extends to the use of the compounds of general formula I to improve and/or restore skin hydration (Bissett D L. *J. Cosmet. Dermatol.* 2006 Dec. 5 (4): 309-15. Glucosamine: an ingredient with skin an dother benefits).

4.5.1 Assay Protocol for Hyaluronidase Activity

Hyaluronidase activity is measured by the assay of residual hyaluronic acid (HA). The substrate is fixed to a carrier then placed in the presence of an enzyme and a quantity of compound to be tested. The residual HA i.e. the non-hydrolyzed HA is assayed using a HA-Elisa detection system: Hyaluronan enzyme-linked immunosorbent assay (Echelon Biosciences®).

0.5 units of hyaluronidase of bovine origin (BTH, Bovine Testis hyaluronidase) were pre-incubated at 37° C. with the compound to be tested. This mixture was deposited on the HA fixed to the surface of a microplate well. The enzymatic reaction took place at pH 7.2n at 37° C. Washing was followed by a recognition step of residual HA by hyaluronectin (NH). The quantity of bonded NH was measured by ELISA using an anti-NH antibody conjugated with alkaline phosphatase. The p-nitrophenyl phosphate disodium salt (pnNpp) substrate of the phosphatase allows spectrometric detection at 405 nm. (Delpech B et al., *Analytical Biochemistry* 149, 555(565 (1985); Robert Stern et al. Analytical Biochemistry 251, 263-269 (1997)). OD intensity was correlated with the quantity of residual HA. The quantity of residual HA is directly linked to enzymatic activity. In the presence of an inhibitor, the larger the quantity of residual HA the more the sample is inhibiting. A percentage inhibition of hyaluronidase will be expressed.

Therefore the net enzymatic activities were calculated which represent the difference in mean gross activity without enzyme and the gross activity of the enzyme with or without the compound to be tested.

The percentage enzymatic inhibition related to the compound to be tested was calculated as follows: % inhibition= (Maximum net enzymatic activity)−Net enzymatic activity in the presence of the compound to be tested)/Maximum net enzymatic activity.

where the maximum net enzymatic activity represents the mean net enzymatic activity of 0.5 U.

4.5.2 Result of the Assay of Hyaluronidase Activity

TABLE 4

Measurement of enzymatic inhibition at different doses (mean as a percentage)

| Concentration | Molecule 1 | Molecule 4 | Molecule 5 | Molecule 6 | 6-ascorbyl palmitate | Ascorbic acid |
|---|---|---|---|---|---|---|
| 500 μM | 122 | * | * | * | * | 4 |
| 250 μM | 119 | * | * | * | 112 | * |
| 200 μM | * | * | * | * | 79 | * |
| 150 μM | * | * | * | * | * | * |
| 100 μM | 113 | * | * | * | 73 | 1 |
| 50 μM | 76 | 111 | 76 | 106 | 71 | * |
| 40 μM | 86 | * | * | * | * | * |
| 30 μM | 66 | * | * | * | * | * |
| 25 μM | 46 | * | * | * | 57 | * |
| 20 μM | 44 | * | * | * | * | * |

TABLE 4-continued

Measurement of enzymatic inhibition at different doses (mean as a percentage)

| Concentration | Molecule 1 | Molecule 4 | Molecule 5 | Molecule 6 | 6-ascorbyl palmitate | Ascorbic acid |
|---|---|---|---|---|---|---|
| 10 µM | 21 | 72 | 31 | 34 | 31 | * |
| 5 µM | 14 | * | * | * | * | * |

* Non-determined

The results of these tests (Table 4) show that vitamin C, used at these concentration (100 and 500 µM) has no effect on hyaluronidase (BTH).

The results of these tests show that 6-ascorbyl palmitate advantageously inhibits hyaluronidase, from 10 to 250 µM, with dose effect.

The molecules 1, 4, 5 and 6 of 5 µM to 500 µM strongly inhibit hyaluronidase: molecule 1 has a dose effect and its IC50 is in the region of 25 to 30 µM.

Molecules 1, 4, 5 and 6 are equivalent to or more active than ascorbyl palmitate which is considered to be the reference molecule (A. Botzki et al, JBC Vol. 279 N°44, pp 45990-450007).

The results of these tests show that the inhibition of hyaluronidase by molecules 1, 4, 5 and 6 is equivalent to or greater than that of ascorbyl palmitate and vitamin C. The anti-hyaluronidase activity of the described molecules is therefore greater than that of ascorbic acid and 6-ascorbyl palmitate.

The present invention therefore concerns the use of the compounds of general formula I for the prevention and/or treatment of skin ageing and to improve and/or restore skin hydration.

4.6.1 Protocol for In Vitro Stimulation of the Proliferation of Dermal Papilla Cells Human dermal papilla cells (Promocell) were placed in culture and held in early passage culture in DMEM medium supplemented with 10% FCS. They were then seeded in a 96-well plate in DMEM medium supplemented with 10% FCS for 12 h. The culture medium was replaced by serum-free DMEM medium then by DMEM supplemented with 1% FCS and molecules 1, 2, 3 and 4 at the different tested concentrations After incubation for 60 h, cell proliferation was evaluated by incorporation of BrdU.

4.6.2 Results of In Vitro Stimulated Proliferation Test of Dermal Papilla Cells

The diagrams in appended FIG. 1 show the increase in BrdU incorporation and the stimulated cellular proliferation of the cells in the presence of the different molecules (as a percent of the control).

Molecule 1 stimulates proliferation of the cells of the dermal papilla with dose effect and best activity at the concentration of 12.5 µM (169% proliferation). Similarly, molecule 4 induces proliferation with stimulation of 113.9% at the concentration of 6.25 µM. Molecules 2 and 3 also induce proliferation of the cells but to a lesser extent than molecules 1 and 4.

The present invention also concerns the use of the compounds of general formula (I) for stimulating re-growth of head and/or body hair.

4.7.1 Protocol for Stimulation of the Growth of the Human Hair Follicle

Biopsies of the occipital region of a human scalp were obtained from operative waste. The hair follicles were isolated by micro-dissection under binocular magnification. They were individually placed in culture following Philpott's technique (Philpott M P et al, J Cell Sci. 97:463-471, 1990). The hair follicles in anagen phase were incubated in 24-well culture dishes in the presence of William's medium supplemented with 10 µg/mL Insulin, 10 µg/mL Transferrin, 10 ng/mL Hydrocortisone, 1 mM Glutamax I, 100 U/mL Penicillin, 100 µg/mL Streptomycin, 250 ng/mL Amphotericin B and in the presence of molecules 3 or 4 for 11 days. The incubation medium was regularly renewed. The lengthening (in µm) of each hair follicle was measured at 4 and 8 days' culture in captured images of the hair follicles.

4.7.2 Results of the Test for Stimulated Growth of the Human Hair Follicle

Figure 2:
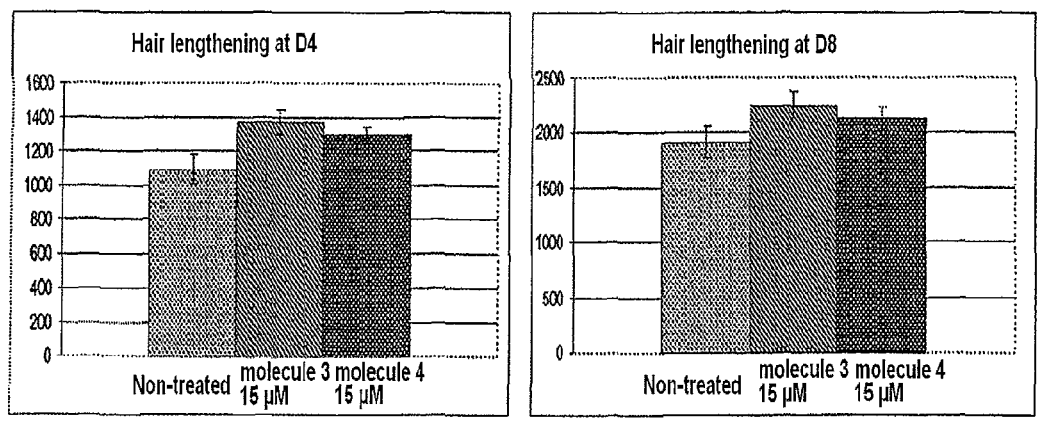
FIG. 2 shows lengthening of hair follicles at day 4 in the left column and at day 8 in the right column.

The diagrams in appended FIG. 2 show the effect of molecules 3 and 4 on the lengthening of hair follicles after incubation for 4 days and for 8 days.

The following table (Table 5) gives the growth percentages obtained for each treatment condition and the percentages for stimulated hair growth obtained with molecules 3 and 4 compared with the control.

TABLE 5

Growth percentages and hair growth stimulation percentages

| | Incubation days | | | |
|---|---|---|---|---|
| | D4 % growth | D8 % growth | D4 % activity | D8 % activity |
| Non-treated | 44 | 77 | 0 | 0 |
| Molecule 3 | 52 | 85 | 25 | 18 |
| Molecule 4 | 51 | 84 | 19 | 12 |

Molecules 3 and 4 at the concentration of 15 µM, significantly stimulate hair growth with 25% and 19% stimulated growth respectively, after 4 days' culture.

The present invention also concerns the use of the compounds of general formula (I) to stimulate the re-growth of head and/or body hair.

4.8.1. Protocol for Evaluation of Hair Bulb Degeneration

The degeneration of the follicle when kinetics cease after 11 culture days, is evaluated by observation of morphological damage of the hair bulb (rounding, deformation). The percentage apoptosis is calculated by counting the number of apoptotic hair follicles relative to the total number of follicles 4.8.2 Results of the Evaluation of Hair Bulb Degeneration The following table (Table 6) shows the effect of molecule 4 on the survival of hair follicles after an incubation time of 11 days.

TABLE 6

Survival of hair follicles after 11 days of incubation
Number of apoptotic bulbs at D11
(Number of total follicles)

| | | Number | % apoptosis |
|---|---|---|---|
| Control | | 9 (12) | 75 |
| Molecule 4 | 15 µM | 6 (12) | 50 |

Molecule 4 allowed marked limiting of hair degeneration (50% of apoptotic hair versus 75% for the control). Therefore, molecule 4 appears to have an anti-apoptosis effect allowing hair survival to be maintained.

The present invention also concerns the use of the compounds of general formula (I) to stimulate re-growth of head and/or body hair.

The invention claimed is:

1. A composition for topical administration, said composition comprising at least 0.01% to 10% by weight of a compound selected from the group consisting of

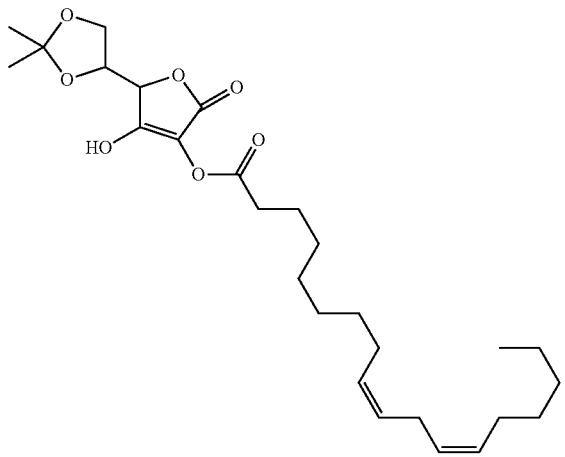

and

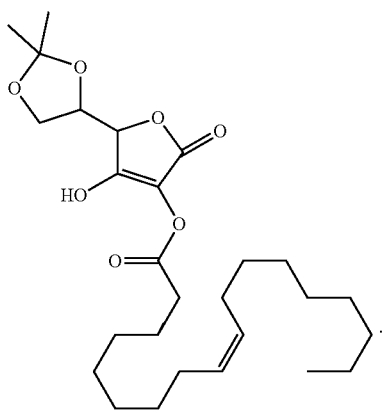

2. The composition for topical administration of claim 1, wherein the compound is:
(9Z, 12Z)-5-(2,2-dimethyl-1,3-dioxolan-4-yl)-4-hydroxy-2-oxo-2,5-dihydrofuran-3-yl octadeca-9,12-dienoate.

3. The composition for topical administration of claim 1, for use thereof as medication or as cosmetic active ingredient.

4. The composition for topical administration of claim 1, for use as a depigmenting active ingredient, anti-age active ingredient, hydrating active ingredient, anti-inflammatory active ingredient, active ingredient for stimulating re-growth of head and/or body hair, or anti-oxidant active ingredient.

5. The composition for topical administration according to claim 1, wherein it is intended for depigmenting the skin and/or head hair and/or body hair, for the treatment of skin ageing, for hydrating the epidermis, for stimulating re-growth of head and/or body hair, or for the treatment of skin inflammation.

6. The composition for topical administration according to claim 1, wherein it comprises from 0.1% to 5% by weight of a compound selected from the group consisting of

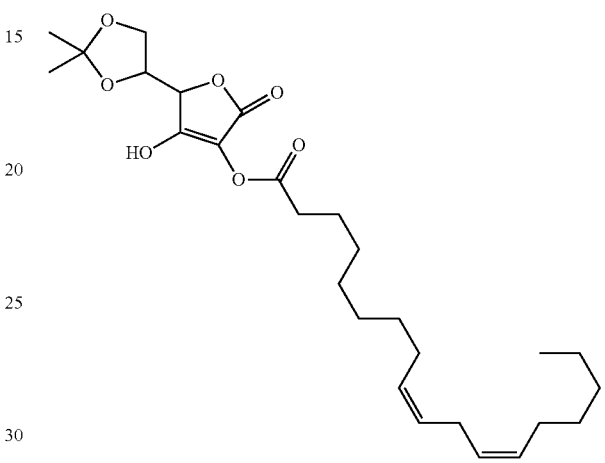

and

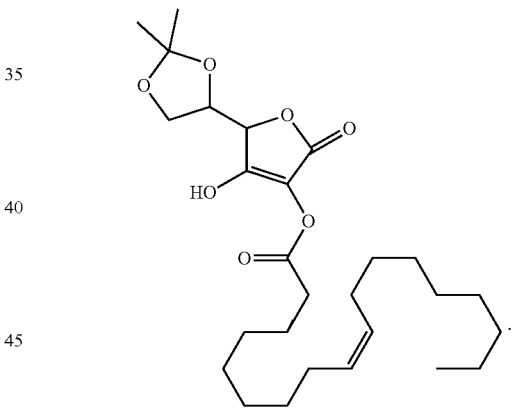

* * * * *